United States Patent
Gerber et al.

(10) Patent No.: US 12,201,374 B2
(45) Date of Patent: Jan. 21, 2025

(54) SYSTEM FOR DETERMINING PROXIMITY OF A SURGICAL TOOL TO KEY ANATOMICAL FEATURES

(71) Applicant: Universitat Bern, Bern (CH)

(72) Inventors: Kate Gerber, Bern (CH); Nicolas Gerber, Bern (CH); Stefan Weber, Boll (CH); Juan Anso, Bern (CH); Tom Williamson, Bern (CH)

(73) Assignee: Universitat Bern, Bern (CH)

( * ) Notice: Subject to any disclaimer, the term of this patent is extended or adjusted under 35 U.S.C. 154(b) by 172 days.

(21) Appl. No.: 16/328,648

(22) PCT Filed: Sep. 4, 2017

(86) PCT No.: PCT/IB2017/055312
§ 371 (c)(1),
(2) Date: Feb. 26, 2019

(87) PCT Pub. No.: WO2018/042400
PCT Pub. Date: Mar. 8, 2018

(65) Prior Publication Data
US 2021/0282864 A1    Sep. 16, 2021

Related U.S. Application Data

(60) Provisional application No. 62/383,460, filed on Sep. 4, 2016.

(51) Int. Cl.
*A61B 34/20* (2016.01)
*A61B 5/00* (2006.01)
(Continued)

(52) U.S. Cl.
CPC ............ *A61B 34/20* (2016.02); *A61B 5/0538* (2013.01); *A61B 5/296* (2021.01); *A61B 5/389* (2021.01);
(Continued)

(58) Field of Classification Search
CPC .. A61B 34/20; A61B 2034/2046–2074; A61B 2034/301–306; A61B 34/32–77
See application file for complete search history.

(56) References Cited

U.S. PATENT DOCUMENTS 9,125,690 B2 * 9/2015 Wohlgemuth ......... A61B 34/30

OTHER PUBLICATIONS

Anso et al. "A Neuromonitoring Approach to Facial Nerve Preservation During Image-guided Robotic Cochlear Implantation" Otology & Neurotology 37:89-98, 2015. (Year: 2015).*

(Continued)

*Primary Examiner* — Angela M Hoffa
(74) *Attorney, Agent, or Firm* — JD Patent & Trademark Ltd.; Julian D. Forman (57) ABSTRACT

Multi-component systems and methods for determining the proximity of surgical tools to key anatomical features are provided. The inventive systems and methods can be applied in any surgical procedure requiring precision to avoid damage to key anatomical features such as nerves, with a particular example being the robotic cochlear implantation minimally invasive approach to cochlear implantation. Use of purpose built surgical robots, electromyography and tissue impedance, stereotactic tracking and drilling force/bone density measurements are all key components, with inputs from these various modalities being dynamically weighted. In the example of robotic cochlear implantation, the inventive concepts are used to provide key surgical guidance so as to avoid damage to the facial nerve and the chorda tympani, among other anatomical features.

14 Claims, 7 Drawing Sheets

(51) Int. Cl.
- *A61B 5/0538* (2021.01)
- *A61B 5/296* (2021.01)
- *A61B 5/389* (2021.01)
- *A61B 34/00* (2016.01)
- *A61B 34/30* (2016.01)
- *A61B 90/00* (2016.01)
- *A61B 90/10* (2016.01)
- *A61F 11/20* (2022.01)

(52) U.S. Cl.
CPC ............ *A61B 5/4893* (2013.01); *A61B 34/25* (2016.02); *A61B 34/30* (2016.02); *A61B 90/10* (2016.02); *A61F 11/20* (2022.01); *A61B 2034/2051* (2016.02); *A61B 2034/2055* (2016.02); *A61B 2034/2061* (2016.02); *A61B 2090/0818* (2016.02); *A61B 2562/0257* (2013.01)

(56) References Cited

OTHER PUBLICATIONS

Williamson et al. "Estimation of Tool Pose Based on Force-Density Correlation During Robotic Drilling" IEEE Transactions on Biomedical Engineering, vol. 60, No. 4, Apr. 2013, pp. 969-976. (Year: 2013).*

Bell et al. "In Vitro Accuracy Evaluation of Image-Guided Robot System for Direct Cochlear Access" Otology & Neurotology 34:1284-1290, 2013. (Year: 2013).*

Caversaccio et al. "Robotic cochlear implantation: surgical procedure and first clinical experience" Acta Oto-Laryngologica, 2017. vol. 137, No. 4, 447-454. (Year: 2017).*

Weber et al. "Minimally invasive, robot assisted cochlear implantation" 2013, 4 pages. (Year: 2013).*

Danilchenko et al. "Robotic Mastoidectomy" Otol Neurotol. Jan. 2011 ; 32(1): 11-16, 12 pages. (Year: 2011).*

Panara et al. "Robotics for Cochlear Implantation Surgery: Challenges and Opportunities" Otol Neurotol 42:e825-e835, 2021. (Year: 2021).*

Weber et al. "Image Guided and Robotic Assisted minimally Invasive Cochlear Implantation" The Hamlyn Symposium on Medical Robotics (2013), 2 pages. (Year: 2013).*

Yoo et al. "A Cadaver Study of Mastoidectomy Using an Image-Guided Human Robot Collaborative Control System" Laryngoscope Investigative Otolaryngology 2: Oct. 2017, 7 pages. (Year: 2017).*

Zagzoog et al. "State of Robotic Mastoidectomy: Literature Review" World Neurosurg. (2018) 116:347-351. (Year: 2018).*

\* cited by examiner

SYSTEM FOR DETERMINING PROXIMITY OF A SURGICAL TOOL TO KEY ANATOMICAL FEATURES

CROSS-REFERENCE TO RELATED APPLICATIONS

This is a U.S. National Stage of International Application PCT/IB2017/055312, filed Sep. 4, 2017, which claims the benefit of U.S. Provisional Application No. 62/383,460, filed Sep. 4, 2016.

FIELD OF THE INVENTION

The present invention relates to the field of multi-component systems and methods for determining the proximity of surgical tools to key anatomical features. Specifically, the invention pertains to the use of multiple modalities for monitoring the proximity of surgical tools to anatomical features such as nerves and functional components of body systems during surgery, as a method of reducing risk of damage or compromise to the nerves or functional components. Monitoring modalities can include, but are not limited to, electromyographic and tissue impedance, stereotactic and force/density measurement approaches. More specifically, the multiple modalities of the present invention can be applied to a system and method for reducing risk to the facial nerve and other cranial base anatomical structures during head and neck surgery, such as, for example, surgery for implantation of cochlear implants. Most specifically, the present invention relates to a system and method that combines intraoperative electromyography and tissue impedance monitoring, stereotactic monitoring and real-time force/density drilling measurements during surgery to reduce risk of damage to the facial nerve and other cranial base anatomical structures during a minimally invasive approach to cochlear implantation.

BACKGROUND OF THE INVENTION

Cochlear implantation ("CI") for severe hearing disorders and deafness has been widely used since the 1980's. Research in the field of CI, aimed at increasing effectiveness and safety, has been ongoing, but the basic surgical approach involving a relatively radical mastoidectomy has remained largely unchanged. The mastoidectomy involves accessing the cochlea by surgically cutting a portion of the patient's skull (mastoid bone) to expose delicate internal structures that must be circumvented to reach the cochlea. The mastoidectomy is an invasive and time consuming approach that involves significant patient pain and recovery time and carries with it the attendant risks of open surgery on the cranium.

For these reasons, attention has been paid in recent years to the development of less invasive methodologies. These various methodologies have been based on attempts to find less invasive approach trajectories to obtain access to the cochlea, which must be achieved to allow placement of a cochlear implant. Approaches attempted have included the pericanal and suprameatal, but they have not been widely adopted in surgical practice.

More recently, the technique known as robotic cochlear implantation ("RCI") has garnered significant attention in the literature. The approach involves drilling a small hole directly in the mastoid surface with the aim of producing a small diameter tunnel (in the range of 1.5-2 mm in diameter) providing direct access to a target site on the cochlea. This surgical approach traverses the facial recess and therefore the resultant tunnel passes close to the facial nerve, the chorda tympani, the auditory canal, and the ossicles. Accordingly, the biggest challenge associated with performing an RCI approach to cochlear implantation is avoiding damage to those structures, particularly the facial nerve and chorda tympani. While current surgical practice has accepted the sacrifice of the chorda tympani in a percentage of cases, it is highly undesirable and, in any event, damage to, or physical destruction of, the facial nerve is an unacceptable outcome of CI surgery.

Due to the challenges associated with the RCI approach, various strategies for increasing safety and reducing the incidence of damage to the facial nerve and other structures have been investigated by the current inventors and other groups. None of the known strategies, standing on its own, provides the necessary safety margin for successful RCI procedures.

The use of intraoperative electromyography ("EMG") and tissue impedance ("TI") monitoring is one such strategy. It is well known that the use of the RCI approach results in the surgical drill passing in very close proximity to the facial nerve, in the range of 0.1-1.5 mm. As such, extremely precise neuromonitoring would be required for EMG to have a viable role in risk reduction. Intraoperative neuromonitoring (INM) via EMG is a standard tool in middle ear surgeries for identification and protection of the facial nerve, but it is most commonly and successfully used in standard-approach cases where line of sight to the surrounding anatomy is available to the surgeon, such as revision surgeries and CI cases involving radical mastoidectomy. However, current EMG and TI approaches (free-running or stimulus triggered-EMG) lack the specificity and sensitivity to be used in RCI cases with the surgical drill passing within less than 1 mm of the facial nerve and with no direct visualization of the surrounding anatomy being available to the surgeon.

Electrical impedance is a method used to characterize in-vivo electrical properties of biological tissues. Different living tissues present different resistances to the flow of ionic current in the body. By injecting an electric field between one working and one counter electrode, which ideally are inserted or at least contacting the target tissue, the tissue impedance can be derived. In the last two decades several researchers have studied the use of TI for navigation of surgical tools, e.g. during spine surgery (Bolger et al. 2007; Bolger et al. 2006; Bourlion et al. 2017; Dai et al. 2014), or needle guidance to avoid anaesthesia blocks (Tsui et al. 2008; Bardou et al. 2013; Kalvoy & Sauter 2016).

Electrical impedance spectroscopy (EIS) relies on the characterization of impedance via a large bandwidth of frequencies rather than measuring a single frequency point. An increased number of frequency bands will give a more representative measurement to distinguish tissue types. For example, higher frequencies enter and exit tissue cells, whereas lower frequencies travel through fluids without entering the tissue cells. The clinical application of EIS during needle guidance has been extensively studied by Kalvoy et al. (Kalvoy et al. 2009; Kalvoy et al. 2010; Kalvoy et al. 2011; Hoyum et al. 2010).

As is well known in the art, EMG in cranial base surgeries involves the insertion of an electrode probe to the surgical site to be used in detecting the facial nerve. Recent work aimed at increasing specificity and sensitivity has focused on the investigation of uninsulated vs. insulated probes and monopolar vs. bipolar stimulation strategies. These investigations have produced mixed results, with some improving specificity with an apparent concomitant deficit in sensitivity, or vice versa. Thus, the current inventors have addressed this shortfall and unmet need with an approach to EMG and TI that involves an insulated probe that is deployed with a multimodal (monopolar and bipolar) stimulation protocol (Anso et al., Otology and Neurotology, 2016, the contents of which, along with all other cited references, are hereby incorporated by reference as if reproduced in their entirety herein).

Along with EMG and TI for facial nerve detection, various stereotactic approaches to improved drilling accuracy have been explored in the context of the RCI approach. Improvements in drilling accuracy are required to ensure that the surgical drill is in fact moving along a pre-planned path based upon an analysis of patient-specific anatomy in a minimally invasive approach where direct visualization of the surrounding anatomy is not possible. Investigated approaches have included targeting devices employing stereotactic drilling templates based upon patient anatomy and robot-assisted stereotactic tracking and instrument guidance, but these have failed to provide the drilling accuracy required for the RCI approach wherein close proximity (without direct visualization) to the facial nerve and chorda tympani are a reality.

Accordingly, the present inventors have developed an approach to increased drilling accuracy that incorporates, among other things, improved patient-to-image registration of pre-surgical planning images, precise intraoperative optical tracking, and the use of rigid drilling tools (Bell et al. 2013). This approach has been shown to enhance drilling accuracy to a point that increases the viability of RCI, thus reducing the need for the radical mastoidectomy approach. The use of drilling process and density information for estimating the position of the tool during drilling has been previously described (Williamson et al. 2013). The approach relies on the extraction of density information along the planned drilling path and a plurality of alternative paths from pre-operative imaging data and the comparison of acquired force/torque data with these density vectors. The similarity between force and density at different locations can then be utilized to provide an independent estimation of tool location.

While significant advancements have been made in the safety and viability of RCI due to the above-described approaches, it is not yet common surgical practice due to the fact that none of the known safety-improvement strategies, standing alone, has been shown to provide the requisite level of detection and protection of the facial nerve and other cranial base anatomical structures. For example, Labadie et al. and others have developed various tracking approaches to enhancing safety in minimally invasive CI, but they lack an integrated, process control approach to enhancing safety and, thus, they have so far failed to provide a solution that can be widely adopted clinically. Thus, the present inventors have developed a multi-modal, process-controlled system and method for detecting the position of a surgical drill relative to the facial nerve in order to address this unmet need.

SUMMARY OF THE INVENTION

These aims and other advantages are achieved by a new system and method for determining the proximity of a surgical tool, such as a surgical drill, to key anatomical features, such as the facial nerve, during an RCI procedure.

The inventive system and method incorporate three main features. First, an improved EMG and TI approach to facial nerve detection is deployed that incorporates an insulated probe that is operated with a multimodal (monopolar and bipolar) stimulation protocol. Second, increased drilling accuracy is achieved through stereotactic monitoring comprising improved patient-to-image registration of pre-surgical planning images, precise intraoperative optical tracking, and the use of rigid drilling tools. Finally, force/density bone measurements are used during drilling to provide a redundant method of determining the position of the surgical drill in addition to the information provided by the stereotactic monitoring. The inventive system and method are integrated, and process-controlled, through the use of a processing unit that receives EMG and TI, stereotactic and force/density measurement inputs, assigns a weighting to the inputs based upon a dynamic protocol, and then provides output information regarding proximity to key anatomical structures along with commands controlling the operation of drilling tools and, optionally, a surgical robot.

Thus, according to an embodiment of the current invention, a facial nerve proximity detection system is provided comprising various components including: a surgical robot configured to enable drilling in close proximity to a critical structure such as the facial nerve; an EMG and TI monitoring system comprising a pulse generator, an EMG/TI stimulation probe and a monitoring unit; a first pose measurement system comprising a stereotactic navigation or tracking system configured to track the robot, the drill and the EMG/TI probe relative to a patient's anatomy; a second pose measurement system comprising an apparatus capable of force/density measurements at the drill tip; and a processing or control unit configured to receive inputs from the EMG and TI monitoring system, the first pose measurement system and the second pose measurement system and accordingly to track the robot, EMG/TI probe and the drilling tool and provide command inputs to the robot based upon the tracking information.

According to an alternative embodiment of the present invention, a method of facial nerve proximity detection is provided. The method comprises receiving inputs from a facial nerve proximity detection system at a control unit and using the detection system inputs to track a surgical robot, an EMG/TI probe and a drilling tool and provide command inputs to the robot based upon the tracking information. The facial nerve proximity detection system used in the inventive method comprises various components including: a surgical robot configured to enable drilling in close proximity to a critical structure such as the facial nerve; an EMG/TI monitoring system comprising a pulse generator, an EMG/TI stimulation probe and a monitoring unit; a first pose measurement system comprising a stereotactic navigation or tracking system configured to track the robot, the drill and the EMG/TI probe relative to a patient's anatomy; a second pose measurement system comprising an apparatus capable of force/density measurements at the drill tip; and the aforementioned control unit configured to receive inputs from the EMG/TI monitoring system, the first pose measurement system and the second pose measurement system.

These and other embodiments of the inventive system and method are described in more detail below with reference to the attached figures.

DETAILED DESCRIPTION OF THE INVENTION

The present invention is now described in detail in connection with its various embodiments and with reference to the attached figures.

In a first embodiment, a key anatomical structure proximity detection system, which may optionally be deployed to detect a proximity to a facial nerve in a patient, is provided comprising various components including: a surgical robot configured to enable drilling in close proximity to a critical structure such as the facial nerve; an EMG/TI monitoring system comprising a pulse generator, a stimulation probe and a monitoring unit; a first pose measurement system comprising a stereotactic navigation or tracking system configured to track the robot, the drill and the EMG/TI probe relative to a patient's anatomy; a second pose measurement system comprising an apparatus capable of force/density correlations based upon force measurements at the drill tip and density information from CT data; and a control unit configured to receive inputs from the EMG/TI monitoring system, the first pose measurement system and the second pose measurement system and accordingly to track the robot, EMG/TI probe and the drilling tool and provide command inputs to the robot based upon the tracking information.

Figure 1:
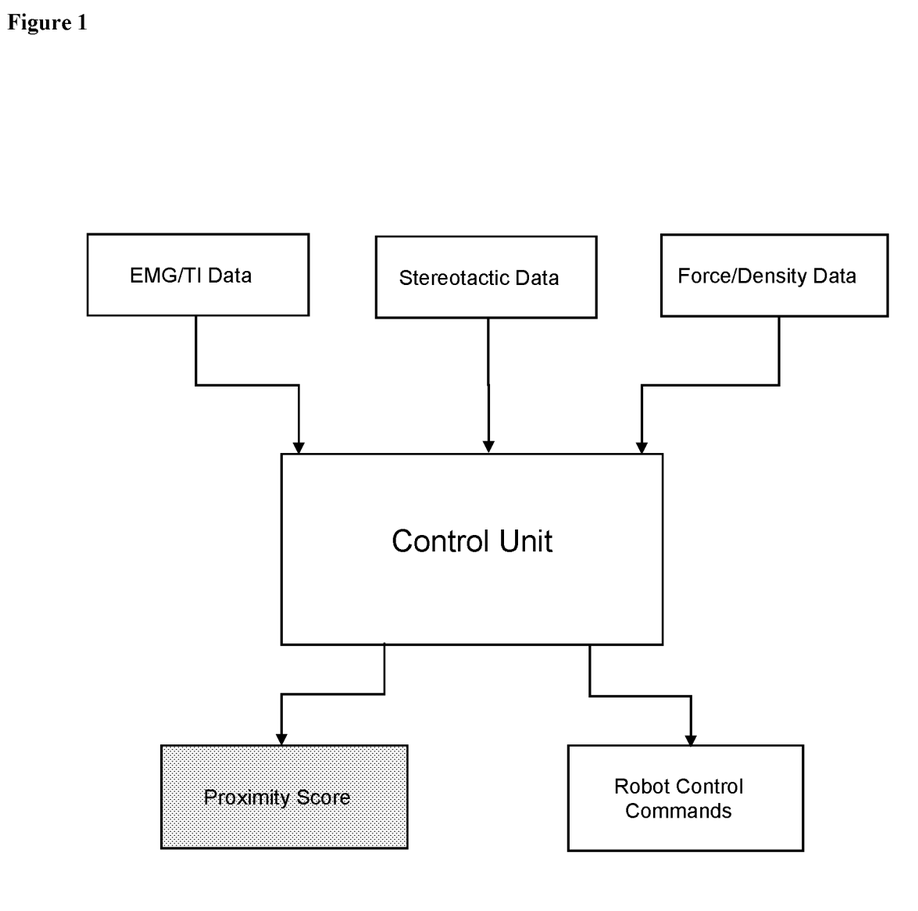
FIG. 1 provides a schematic view of the operation of a control unit according to an embodiment of the present invention.

A schematic of the operation of a control unit according to this embodiment of the invention is found in FIG. 1. As shown in FIG. 1, the control unit receives inputs from the EMG/TI monitoring system and the first and second pose measurement systems, assigns a weight to those inputs based upon a dynamic algorithm, and then provides outputs comprising a "proximity score" assessing the safety margin between the drilling tool and key anatomical features, tracking information pertaining to the tool, the EMG/TI probe and the surgical robot, and commands for the surgical robot based upon the "proximity score" and the tracking information.

The control unit provided in accordance with various embodiments of the present invention operates according to a dynamic algorithm to provide a "proximity score" assessing the safety margin between a surgical instrument and key anatomical features. The control unit algorithm must be dynamic in nature to accommodate the fact that different input streams should be weighted differently during different phases of a surgical procedure in order to provide the necessary safety margin between a surgical instrument and various aspects of a patient's anatomy. It is this process control approach provided by the present inventors, with its resultant integration of multiple tracking modalities that distinguishes the present invention from prior approaches using single tracking modalities or perhaps multiple modality approaches that nevertheless lack the opportunity for real-time feedback from the surgical field and adjustments to positioning of surgical instruments.

In the context of an RCI procedure, and in accordance with an embodiment of the present invention, the control unit receives inputs from an EMG/TI probe, a stereotactic navigation or tracking system and a drilling system capable of force density correlations based upon force measurements at the drill tip and density information from CT data. Each of these modalities provides critical information for assessing the safety margin between a drilling tool and key anatomical features such as the facial nerve and the chorda tympani. However, as described above, none of the modalities operating alone provides a sufficient safety margin and, in addition, each of the modalities provides a different quality and relevance of information at different stages of an RCI procedure. Accordingly, a dynamic, process-control approach is required to provide a "proximity score" assessing the safety margin between the drilling tool and the various anatomical features.

Solely by way of example, in an RCI procedure, stereotactic tracking comprising optical and mechanical approaches and based upon, inter alia, preoperative planning and intraoperative patient-to-image registration, has a high level of importance early in the procedure when the surgeon is making decisions regarding the entry point, positioning and pose of the surgical drill. Tracking based upon preoperative (and perhaps intraoperative) imaging data can maintain a high level of importance throughout the procedure, along with mechanical tracking of the surgical tool by way of the surgical robot. However, the inadequacy of stereotactic approaches alone requires the addition of EMG/TI data and force/density measurement data.

EMG is a well-known approach for assessing proximity to the facial nerve but is not particularly effective if drilling in bone at distances greater than 3 mm from the nervous system structure of interest and is most effective at even closer distances. Thus, in an RCI procedure according to the present invention, the EMG/TI probe would be deployed at a point where the preoperative image data, patient-to-image registration and mechanical tracking suggest that an appropriate proximity to the facial nerve has been achieved. EMG/TI inputs to the control unit would then be increasingly highly weighted as all of the available data suggests greater and greater physical proximity of the drilling tool to the facial nerve. In this way, EMG/TI data suggesting proximity of the tool to the facial nerve would be weighted differently when all available data suggested a distance of 3 mm from the structure than would data suggesting tool proximity to the facial nerve when all available data suggested a distance of less than 1 mm from the structure. Solely by way of example, the former data might be lightly weighted and implicitly regarded as a false positive whereas the latter would be highly weighted and would likely result in a high "proximity score" and a command to the drilling tool (through the surgical robot) to stop drilling until safety could be verified.

Force/density correlations are another example of data that must be treated dynamically during an RCI procedure to provide a valid and reliable input to a "proximity score." Density (and resulting drilling force) of the structures being penetrated by the surgical drill during the procedure display both high inter and intra-patient variability. Thus, while it is possible to estimate tool pose based upon correlating drilling force to preoperative imaging data, the estimation of tool pose becomes more reliable over time during the procedure as the surgical robot "learns" based upon the continual stream of force/density information received at the control unit. The learning function is based upon the fact that preoperative imaging data provides a large number of possible drilling trajectories, each with its own bone density profile. As the surgical procedure proceeds, if a force/density measurement suggests that the drilling tool is not on the desired path, the processing component of the control unit will compare the force/density data to a large number of adjacent drilling trajectories until it finds the most likely candidate for the current position of the drilling tool. One of skill in the art will realize that the set of possible trajectories will be very large at the beginning of the procedure, thus resulting in unreliable pose estimation data, but the set will narrow as the procedure progresses, resulting in a continual enhancement of the reliability of the data. Solely by way of example, the force/density measurements tend to be an unreliable method of estimating tool pose (and therefore an unreliable input to a "proximity score") during the first few millimeter of drilling, but become more reliable upon closer proximity to the facial nerve and the ultimate access point to the cochlea. Accordingly, the dynamic "proximity score" algorithm will generally attach a lower weight to the force/density measurements early in the procedure and a higher weight as the procedure progresses.

Figure 2:
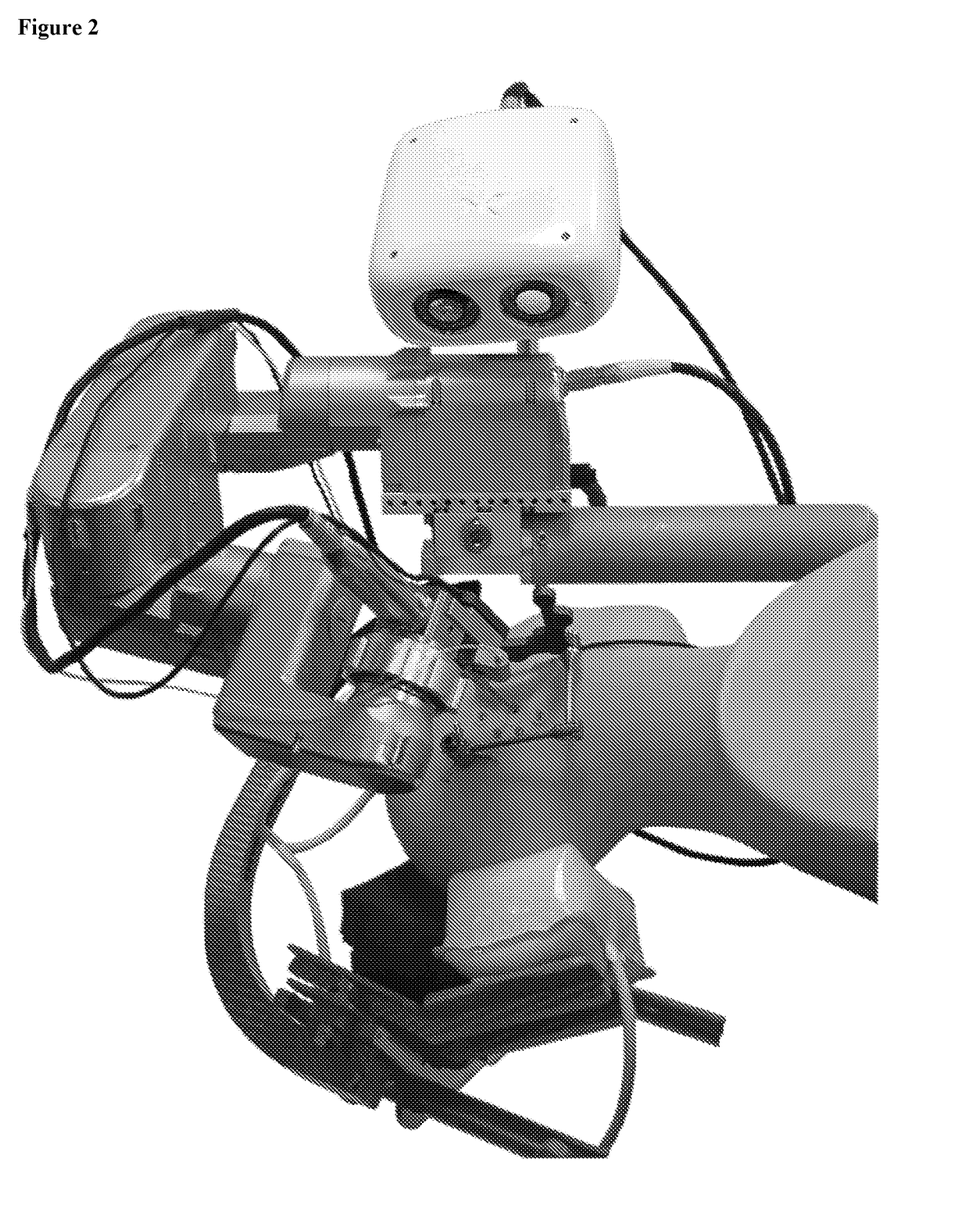
FIG. 2 is a representative depiction of a surgical robot used in accordance with various embodiments of the present invention.

A surgical robot in accordance with the present invention is configured similarly to one described in an academic paper by some of the present inventors entitled "In Vitro Accuracy Evaluation of Image-Guided Robot System for Direct Cochlear Access," Otology and Neurotology 2013, the contents of which are hereby incorporated by reference as if fully reproduced herein. A representative figure of a surgical robotic system provided in accordance with the present invention and in use during a CI procedure is found at FIG. 2.

Figure 3:
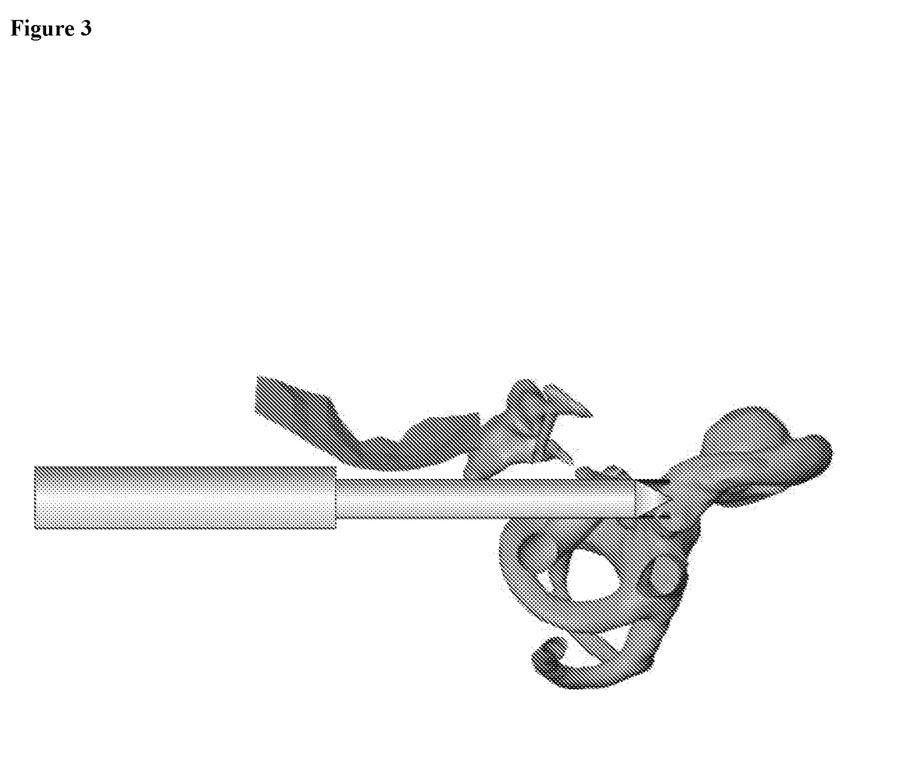
FIG. 3 is a schematic of a planned surgical drilling trajectory based upon preoperative imaging data in accordance with an embodiment of the present invention.

A first pose measurement system according to the present invention is also described in the above mentioned paper. Specifically, the stereotactic approach comprises the use of fiducial screws, preoperative planning based upon imaging, patient-to-image registration and drilling with optical and mechanical tracking. The fiducial screws are used to provide a template for insertion of the drilling tool, preoperative imaging provides a plan for progressing the surgical tool to the target on the cochlea, patient-to-image registration ensures that the tool is progressing along the planned path during the RCI procedure and mechanical tracking of the surgical tool through the robot provides an additional safety measure. FIG. 3 shows a schematic of a preoperative plan of a drilling trajectory based upon imaging data in accordance with an embodiment of the present invention. The trajectory shows the relatively narrow safe path to the cochlea traversing the facial recess. The various integrated, process-controlled tracking modalities provided by the present inventors will alert the surgeon to deviations from the planned trajectory that endanger the nearby critical structures.

Figure 4:
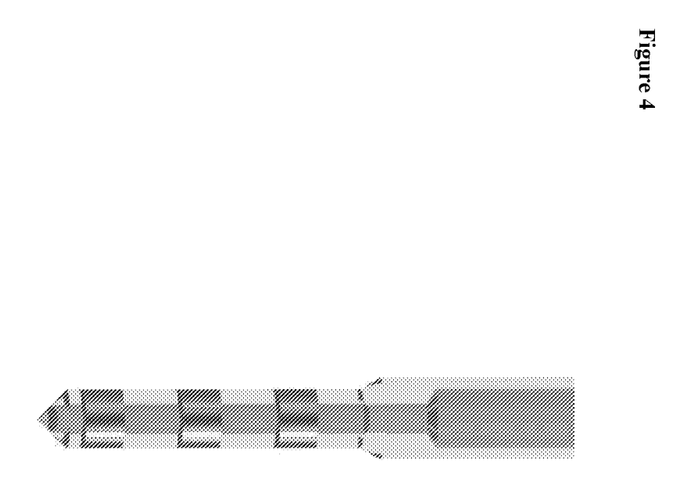
FIG. 4 is a representative depiction of an EMG/TI probe used in accordance with the present invention.

An EMG/TI monitoring system according to an embodiment of the present invention is described in "A Neuromonitoring Approach to Facial Nerve Preservation During Image-Guided Robotic Cochlear Implantation," Otology and Neurotology 2016, also authored by some of the present inventors, the contents of which are also hereby incorporated by reference as if fully reproduced herein. Accordingly, an insulated probe is provided that is deployed with a multimodal (monopolar and bipolar) stimulation protocol in order to achieve the sensitivity and specificity required for the RCI application. A representative depiction of such a probe is provided at FIG. 4 showing its various component anode and cathode structures. Pulses with varying durations and amplitudes are used to estimate proximity to the facial nerve based on stimulus threshold values derived from positive EMG/TI responses. According to this embodiment, the inventors contemplate a probe that is capable of operating both as a electromyography stimulation probe and a tissue impedance measurement probe. However, one of skill in the art will readily understand that the electromyography and tissue impedance measurement functions could be carried out by separate probes. The present inventors have disclosed a probe with electromyography and tissue impedance functions for ease of use during surgical procedures.

The EMG/TI probe in accordance with the present invention provides both EMG and TI data to be analyzed by the control unit. In the case of TI data, electrical impedance spectroscopy can be used to discriminate tissue types in close proximity to (or in contact with) the probe in view of the obtained TI data. In the context of an RCI procedure, a surgical trajectory passing laterally (and safely) with respect to the facial nerve or other critical structures will travel a path consisting mostly of different bone densities (e.g., cancellous, cortical, air cells). In contrast, an unsafe RCI surgical trajectory that approaches the facial nerve or other critical structure would encounter bone tissue, but likely also cerebrospinal fluid and, eventually, nerve tissue. Thus electrical impedance spectroscopy analysis of TI data can discriminate tissue types and provide a redundant indicator of facial nerve (or other critical structure) proximity independent of EMG and other navigation or tracking modalities.

Figure 5:
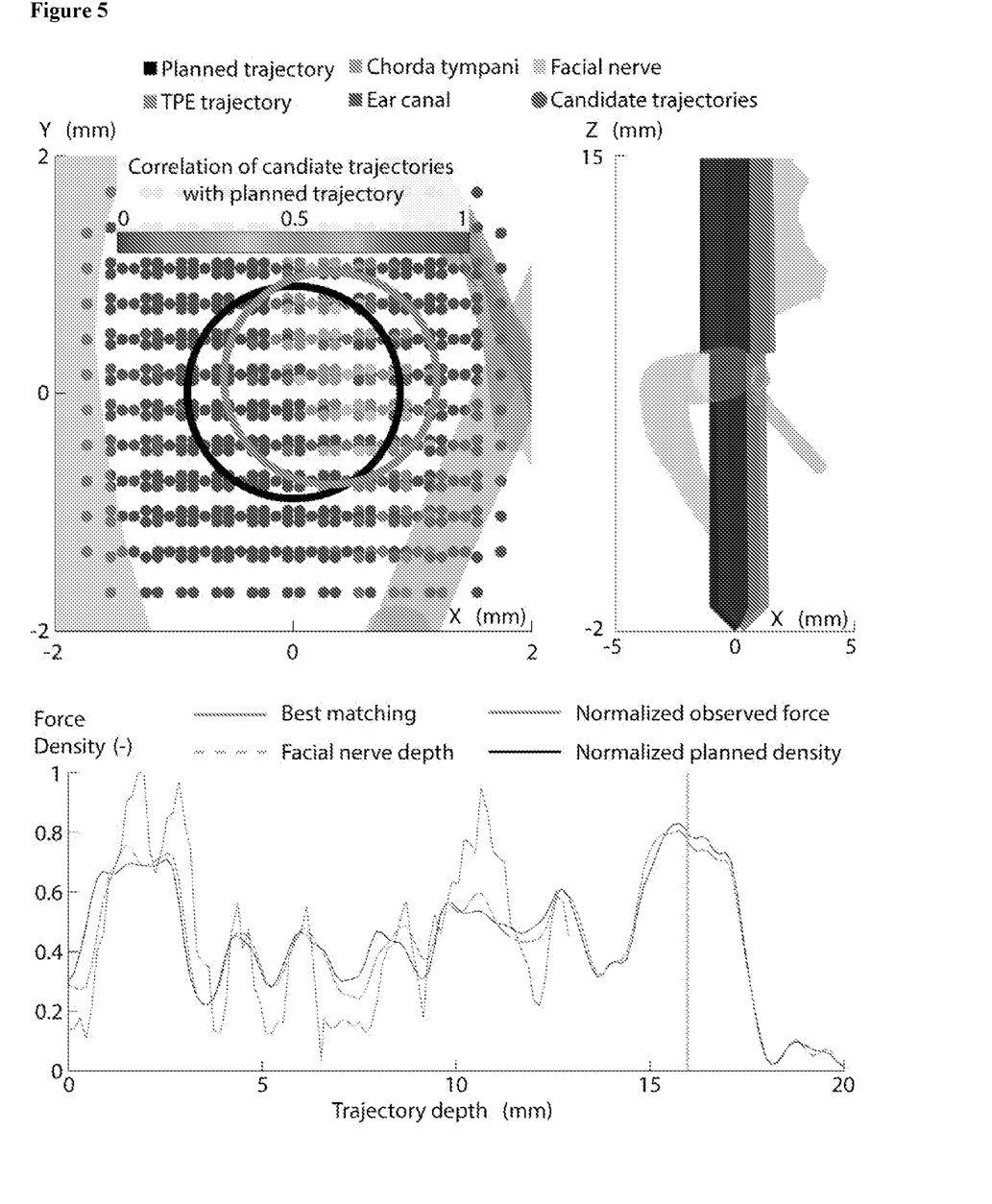
FIG. 5 is a schematic of planned and alternate surgical drilling trajectories based upon force/density data in accordance with an embodiment of the present invention.

Finally, a second pose measurement system capable of force density measurements at the drilling tip is described in "Estimation of Tool Pose Based on Force-Density Correlation During Robotic Drilling," TBME-00737-2012, the contents of which are also hereby incorporated by reference as if fully reproduced herein. As discussed above with reference to the weighting of inputs to the control unit, the estimation of the pose of a drilling tool with force/density measurements begins with preoperative imaging of the patient's anatomy resulting in a set of candidate bone density profiles sampled around the planned trajectory. During the procedure, drilling force is measured by known methods based upon feedback to the drilling tool and positioning is estimated based upon correlation of measured force to density values provided by the preoperative imaging data. If the force/density measurement differs from that estimated on the planned drilling trajectory, the processing component of the control unit compares the actual measurements to a universe of possible trajectories to determine the tool's position in three-dimensional space. Adjustments can then be made to surgical approach, taking into account the appropriate weighting of the force/density measurements depending on the stage of the surgical procedure. FIG. 5 provides a schematic representative of planned and alternative drilling approaches based upon force/density data.

Similarly, in another embodiment of the present invention, a method of facial nerve proximity detection is provided. The method comprises receiving inputs from a facial nerve proximity detection system at a control unit and using the detection system inputs to track a surgical robot, an EMG/TI probe and a drilling tool and provide command inputs to the robot based upon the tracking information. The facial nerve proximity detection system used in the inventive method comprises various components including: a surgical robot configured to enable drilling in close proximity to a critical structure such as the facial nerve; an EMG/TI monitoring system comprising a pulse generator, a stimulation probe and a monitoring unit; a first pose measurement system comprising a stereotactic navigation or tracking system configured to track the robot, the drill and the EMG/TI probe relative to a patient's anatomy; a second pose measurement system comprising an apparatus capable of force/density measurements at the drill tip; and the aforementioned control unit configured to receive inputs from the EMG monitoring system, the first pose measurement system and the second pose measurement system.

In this embodiment, the surgical robot, EMG/TI monitoring system and first and second pose measurement systems are configured as described above. In addition, the method of facial nerve proximity detection is facilitated through the use of a control unit that functions to receive inputs from the EMG/TI monitoring system, the first pose measurement system and the second pose measurement system and accordingly to track the robot, the drilling tool and the EMG/TI probe and provide command inputs to the robot. The control unit functions by producing a score representing proximity to a key anatomical feature such as the facial nerve and it does so by assigning a weight to the data it receives from the EMG/TI monitoring system and the pose measurement systems and producing a composite score. Weighting of input streams is assigned according to the considerations described herein with reference to the inventive system. Accordingly, a method of facial nerve proximity detection is provided by employing a control unit that combines input from multiple methods of proximity detection, thus enhancing the safety of minimally invasive robotic cochlear implantation.

In accordance with another embodiment of the present invention, a method of facial nerve proximity detection is provided that includes the calculation of a facial nerve proximity score based upon inputs received at a control unit from other components of a facial nerve proximity detection system that comprises a surgical robot configured to enable drilling in close proximity to a critical structure such as the facial nerve; an EMG/TI monitoring system comprising a pulse generator, a stimulation probe and a monitoring unit; a first pose measurement system comprising a stereotactic navigation or tracking system configured to track the robot, the drill and the EMG/TI probe relative to a patient's anatomy; and an second pose measurement system comprising an apparatus capable of force/density measurements at the drill tip.

Figure 6:
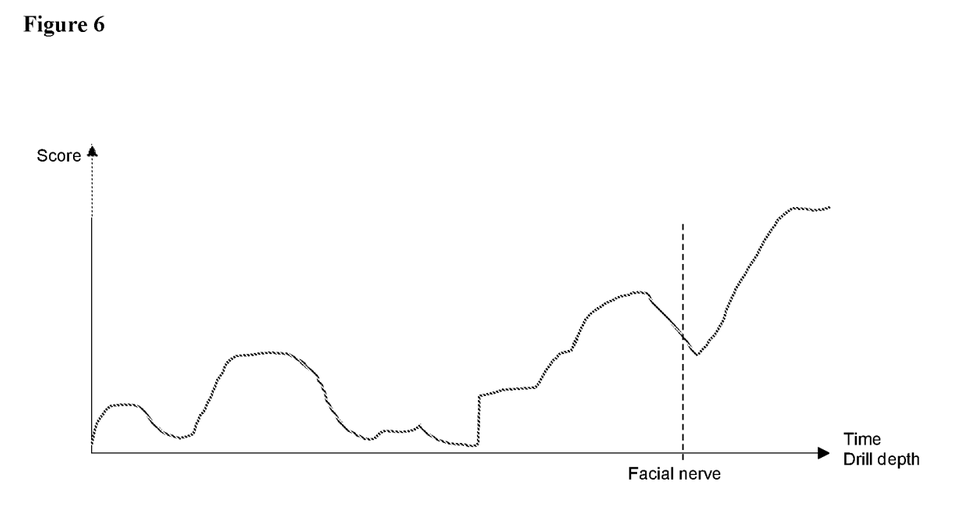
FIG. 6 demonstrates one option for mapping a facial nerve proximity score according to an embodiment of the present invention.

The facial nerve proximity score may be computed and represented in a number of discrete steps or as a continuous value. In other words, the facial nerve proximity score may be computed and represented in discrete steps that individually take into account and present input from the EMG/TI monitoring system, the first post measurement system and/or the second pose measurement system as incremental values, or the facial nerve proximity score can be computed and represented as a cumulative and aggregate measure of all of the aforementioned inputs. Preferably, the computed value can be calibrated and presented to the user as a percentile score [0 . . . 100%] where higher values suggest a higher likelihood of facial nerve injury. Additionally, the individual input values can be presented in addition to the score to help the user understand the data presented and the clinical situation. Furthermore, the percentile score can also be presented graphically as a function of other environmental or situative variables. For example, the percentile score can be mapped in time or as function of drill depth, as exemplified in FIG. 6. Additionally, input signals might also be presented. Here the user benefits from the representation as derivates of the score can be understood better.

The facial nerve proximity score may be computed by weighting the various inputs from, among other things, the EMG/TI monitoring system, the first pose measurement system and the second pose measurement system. The assigned weighting of the inputs used in arriving at the facial nerve proximity detection score will vary with each input according to the quality and reliability of the information being provided by the various inputs, according to the following generalized equation:

$$S_{FNP} = \sum_i w_i(t) \cdot I_i(t)$$

where $I_i(t)$ is an input, with $w_i(t)$ is a weighting factor and $S_{FNP}$ is the facial nerve proximity score.

Fundamentally, weightings consist of a static portion and a dynamic portion that are combined in the computation (summarizing, multiplying) as follows:

$$w_i = w_{dynamic} + w_{static}$$

The dynamic portion of the individual weightings is computed in each cycle and throughout the complete procedure (i.e. over time, in space) by incorporating reliability information of a given measurement (i.e. the signal quality). Lower values for a dynamic weight depict a lower quality of said measurement in that computation cycle.

Figure 7:
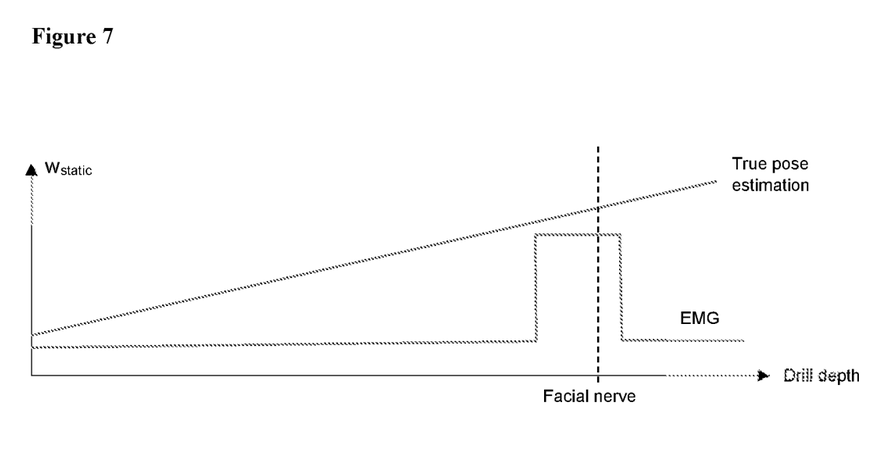
FIG. 7 demonstrates the weighting of input variables to the facial nerve proximity score according to an embodiment of the present invention.

The static portion of the weight is a predefined function, ranging from completely static to more sophisticated functions (slope, quadratic etc.) and decodes the abstract importance of a signal throughout the procedure. Solely by way of example, EMG/TI data from the EMG/TI monitoring system is considered to be the most clinically relevant. In an embodiment, it would be assigned the highest static weighting in an area close to the facial nerve in the overall facial nerve proximity score. Solely by way of example, force/density correlations computed by the second pose measurement system are likely not conclusive because the accuracy and precision of these measurements are generally within the same order of magnitude as the tool-to-critical structure distance being considered (and, therefore, not of high clinical significance) during the early part of an RCI procedure for the reasons discussed herein. Thus, the calculation of a facial nerve proximity score would assign a low static weighting to inputs from the second pose measurement system during early phases of the RCI procedure, but the weighting would increase over the course of the procedure as the force/density data becomes more clinically relevant, as exemplified in FIG. 7.

While this invention has been shown and described with reference to particular embodiments thereof, it will be understood by those of skill in the art that various changes in form and details may be made therein without departing from the spirit and the scope of the invention as defined by the appended claims. Solely by way of example, not by way of limitation, one of skill in the art will easily understand that the inventive system and method may be used for other surgical applications where precise operation of surgical tools and intraoperative monitoring are required to provide requisite safety margins to avoid damage to critical anatomical structures.

What is claimed is:

1. A facial nerve proximity detection system comprising:
   a surgical robot comprising at least one surgical tool operably connected to the surgical robot, the robot being configured to operate near the facial nerve;
   an electromyography system comprising a pulse generator and a stimulation probe connected to the pulse generator functioning to emit pulses from the pulse generator into tissue, and a monitoring unit configured to receive pulse responses from nerves;
   a tissue impedance measurement system comprising a measurement probe and a processing unit to measure tissue impedance near the measurement probe;
   a first pose measurement system comprising a stereotactic surgical tracking system configured to track the surgical robot, the at least one surgical tool, the stimulation probe and the measurement probe relative to a patient;
   a second pose measurement system operating independently of the first pose measurement system configured to track the pose of the at least one surgical tool relative to the patient through non-stereotactic means; and
   a control unit comprising a graphical user interface, configured to acquire inputs from the electromyography and tissue impedance system, the first pose measurement system and the second pose measurement system and produce a weighted facial nerve proximity score based on the inputs from the electromyography system, the tissue impedance measurement system, the first pose measurement system, and the second pose measurement system, to track the robot, the at least one surgical tool, the stimulation probe and the measurement probe relative to the patient, and configured to provide command inputs to a control system of the surgical robot based on the weighted facial nerve proximity score and tracking information so as to avoid the facial nerve.

2. The system of claim 1, wherein the stimulation probe can be either operably connected to the robotic system or operated independently of the robotic system by a human user.

3. The system of claim 1 wherein the stimulation probe is tracked in space through a multitude of pose measurement systems, including an internal mechanical tracking system of the surgical robot and the first pose measurement system and the second pose measurement system.

4. The system of claim 1, wherein the tissue impedance measurement system is externally controllable and programmable such that the electrical impedance of the tissue surrounding the stimulation probe can be measured.

5. The system of claim 1, wherein the pulse generator is externally controllable and programmable such that sequences of pulses varying in amplitude, frequency and pulse width can be generated and emitted through the stimulation probe and wherein the pulse sequences can be dynamically adjusted based on assessment of a feedback signal coming from the monitoring unit.

6. The system of claim 1, wherein the production of the weighted facial nerve proximity score comprises computing a most likely pose of the at least one surgical tool by dynamically weighting the inputs from the electromyography and tissue impedance system, the first pose measurement system and the second pose measurement system.

7. The system of claim 6, wherein the weighted facial nerve proximity score is computed and represented in a number of discrete steps or as a continuous value.

8. The system of claim 1, wherein the control unit provides the command inputs to the control system of the robot in order to prevent the robot from operating at an unsafe distance from the facial nerve.

9. A method of facial nerve proximity detection comprising:
   providing a facial nerve proximity detection system comprising:
      a surgical robot comprising at least one surgical tool operably connected to the surgical robot, the robot being configured to operate near the facial nerve;
      an electromyography system comprising a pulse generator and a stimulation probe connected to the pulse generator functioning to emit pulses from the pulse generator into tissue, and a monitoring unit configured to receive pulse responses from nerves;
      a tissue impedance measurement system comprising a measurement probe and a processing unit to measure tissue impedance near the measurement probe;
      a first pose measurement system comprising a stereotactic surgical tracking system configured to track the surgical robot, the at least one surgical tool, the stimulation probe and the measurement probe relative to a patient;
      a second pose measurement system operating independently of the first pose measurement system configured to track the pose of the at least one surgical tool relative to the patient through non-stereotactic means; and
      a control unit comprising a graphical user interface, configured to acquire inputs from the electromyography and tissue impedance system, the first pose measurement system and the second pose measurement system and produce a weighted facial nerve proximity score based on the inputs from the electromyography system, the tissue impedance measurement system, the first pose measurement system and the second pose measurement system, and configured to provide command inputs to a control system of the surgical robot and to track the robot, the at least one surgical tool, the stimulation probe and the measurement probe relative to the patient;
   receiving the outputs from the electromyography and tissue impedance systems, the first pose measurement system and the second pose measurement system;
   producing the weighted facial nerve proximity score;
   tracking the robot, the at least one surgical tool, the stimulation probe and the measurement probe to obtain tracking information pertaining to the robot, the at least one surgical tool and the measurement probe and the stimulation probe; and
   providing the command inputs to the control system of the surgical robot according to the weighted facial nerve proximity score and the tracking information so as to avoid the facial nerve.

10. The method of claim 9 wherein the stimulation probe is tracked in space through a multitude of pose measurement systems, including an internal mechanical tracking system of the surgical robot and the first pose measurement system and the second pose measurement system.

11. The method of claim 9, wherein the pulse generator is externally controllable and programmable such that sequences of pulses varying in amplitude, frequency and pulse width can be generated and emitted through the stimulation probe and wherein the pulse sequences can be dynamically adjusted based on assessment of a feedback signal coming from the monitoring unit.

12. The method of claim 9, wherein the production of the weighted facial nerve proximity score comprises computing a most likely pose of the probe or tool by dynamically weighting the inputs from the electromyography and tissue impedance system, the first pose measurement system and the second pose measurement system.

13. The method of claim 12, wherein the weighted facial nerve proximity score is computed and represented in a number of discrete steps or as a continuous value.

14. The method of claim 12, wherein the dynamic weighting of inputs changes according to the stage of a robotic cochlear implantation procedure.

* * * * *